US008591837B2

(12) United States Patent
Frey et al.

(10) Patent No.: US 8,591,837 B2
(45) Date of Patent: Nov. 26, 2013

(54) METHOD FOR PRODUCING A MAGAZINE BY INJECTION MOLDING, AND A MAGAZINE FOR AN ANALYSIS DEVICE

(75) Inventors: Stephan-Michael Frey, Griesheim (DE); Hans List, Hesseneck-Kailbach (DE); Andrea Rittinghaus, Neckarsteinach (DE); Maik Schwede, Jena (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 15 days.

(21) Appl. No.: 13/085,743

(22) Filed: Apr. 13, 2011

(65) Prior Publication Data

US 2011/0250093 A1 Oct. 13, 2011

Related U.S. Application Data

(63) Continuation of application No. PCT/EP2009/006885, filed on Sep. 23, 2009.

(30) Foreign Application Priority Data

Oct. 13, 2008 (EP) .................................... 08166497

(51) Int. Cl.
*G01N 21/01* (2006.01)
(52) U.S. Cl.
USPC .......................................... 422/554; 356/246

(58) Field of Classification Search
USPC .......... 356/244, 246; 422/401–407, 500, 502, 422/547, 548, 551, 554, 556
See application file for complete search history.

(56) References Cited

U.S. PATENT DOCUMENTS

| 4,226,531 A * | 10/1980 | Tiffany et al. ................. 356/246 |
| 2006/0064035 A1 | 3/2006 | Wang et al. |
| 2007/0179405 A1 * | 8/2007 | Emery et al. .................. 600/583 |

FOREIGN PATENT DOCUMENTS

| EP | 2130493 A1 | 12/2009 |
| WO | WO 2007/041244 | 4/2007 |

* cited by examiner

*Primary Examiner* — Paul Hyun
(74) *Attorney, Agent, or Firm* — Harness, Dickey

(57) ABSTRACT

Method for the injection-molding production of a magazine having a plurality of chambers, separated by partition walls, including an outer wall formed by an outer wall of the magazine. The method uses a casting mold having an outer wall channel corresponding to the outer wall of the magazine, and partition wall channels corresponding to the partition walls, and a gate opening. A plurality of partition wall channels extend from the gate opening to the outer wall channel. The method comprises injecting a plastic compound into the gate opening. The plastic compound flows from the gate point to the partition wall channels into the outer wall channel. The plastic compound streams have a differing flow speed in alternating partition wall channels so a joint line, which is aligned with a partition wall channel, forms on the outer side of the outer wall channel.

6 Claims, 3 Drawing Sheets

METHOD FOR PRODUCING A MAGAZINE BY INJECTION MOLDING, AND A MAGAZINE FOR AN ANALYSIS DEVICE

CROSS-REFERENCE TO RELATED APPLICATIONS

This application is a continuation of International Patent Application No. PCT/EP2009/006885, filed on Sep. 23, 2009, which claims the benefit and priority of European Patent Application No. 08166497.1, filed on Oct. 13, 2008. The entire disclosures of the above applications are incorporated herein by reference.

BACKGROUND

The present invention relates to a method for the injection-molding production of a magazine for an analysis device. The magazine has a plurality of chambers which are positioned adjacent to one another and are separated from one another by partition walls. They have a chamber outer wall, which is formed by an outer wall of the magazine. The chambers are particularly suitable and adapted for receiving analysis elements, in which an analyte in a body fluid sample can be determined.

SUMMARY

In many fields of medical analysis, analytes are determined in a body fluid sample, in particular in blood, which is obtained through a puncture in the skin of the patient. When the body fluid is taken from a body part, preferably from the fingertip, small quantities are sufficient to determine an analyte, for example, the glucose content in blood, for medical and diagnostic purposes. The devices used may also be readily used by laypeople.

Such devices are used, for example, by diabetics to check their blood sugar content regularly. In order that the monitoring is also actually performed a plurality of times in a day by the patients, in addition to low pain of the puncture, simple and comfortable handling of the devices is necessary. More recent device developments therefore comprise integrated analysis systems, which allow an "one-step treatment". The user must only apply such an automated device once and can then read off the analysis result—without further handling steps.

Analysis elements, e.g., of integrated devices, induce a measurable change as soon as they come into contact with a liquid containing one of the analytes being looked for. This change can be measured electrochemically, two electrodes being in contact with a sample receiving surface of the analysis element. Measuring a current change permits conclusions about the presence and the quantity of an analyte which is looked for.

In addition to electrochemical measurement, optical measurements have be-come established. The contacting of the sample fluid with the analysis element results in an optically measurable change, which is a measure of the presence and the quantitative amount of an existing analyte. An optical evaluation unit must be positioned such that it can scan the analysis element in order to detect the measurable change. The analysis element and the optical measuring unit must be moved relative to one another if necessary.

Since the analysis elements must be stored dry before the analysis, they are typically positioned in magazines, and also frequently in combined magazines which also include the puncture elements. In order to perform an optical measurement, after the sample delivery the analysis element can be moved into a position outside the magazine, so that unobstructed optical scanning is possible. A movement of the analysis element in addition to the puncture element is mechanically more complex, however. Therefore, the analysis element is preferably left in the magazine and the measuring optic is positioned so that optical detection is possible through the magazine wall. The magazine must be implemented as transparent as possible, so that no interference with the optical evaluation occurs, which could influence the measurement result.

Therefore it is an object of the present invention is therefore to propose a magazine having improved properties, in particular a magazine having optimized optical properties, which allows an optical analysis of an analysis element in the magazine.

The present object is achieved by a method for the injection-molding production of a magazine having the features of claim 1 and by a magazine having the features of claim 10.

A magazine having a plurality of chambers, which are preferably oriented in the same direction, is specified by the method according to the invention for injection-molding production. The chambers of the magazines are separated from one another by partition walls. They have a chamber outer wall, which is formed by the outer wall of the magazine. A casting mold, which has a gate point having a gate opening, an outer wall channel, and partition wall channels, is used to produce such a magazine. The outer wall channel of the casting mold corresponds to the outer wall of the magazine to be produced. The partition wall channels correspond to the partition walls between the chambers of the magazine. The partition wall channels are oriented in such a manner that they extend from the gate point to the outer wall channel.

The method according to the invention comprises the following steps. A plastic compound, which is transparent at least after curing, is injected into the gate opening of the casting mold. This is performed using injection-molding technology at a predetermined pressure and a defined temperature. The pressure and temperature typically depend on the plastic compound used. In a further step, the plastic compound is caused to flow as a plastic compound stream from the gate point through the partition wall channels into the outer wall channel in such a manner that the plastic compound streams have a differing flow speed in alternating partition wall channels. The flow speed is different in at least two adjacent channels, the speed preferably in turn being equal in each second channel. The plastic compound thus reaches the end of the partition wall channels at different rates, as a function of the flow speed prevailing therein.

In a further step, the plastic compound streams flow together at the end of the partition wall channels into the outer wall channel in such a manner that a joint line forms on the outer side of the outer wall channel. This joint line, which is also referred to as a flow line, arises through the meeting of two plastic com-pound streams. The joint line is not only formed on the outer side of the outer wall channel, but rather forms a plane in which the plastic streams meet. The surface normal of the plane is either oriented (essentially) perpendicular to the partition wall channels or—in the case of drum-shaped casting molds—oriented perpendicular to a radially extending line.

The location of the meeting of two plastic compound streams may be arbitrarily specified by the control of the flow speeds in the partition wall channels. It is important that the joint line is not formed in the area of the outer wall channel which is used for an optical measurement of a measured variable in the interior of the magazine. The flow speed of the plastic compound streams is there-fore set in such a manner that it differs in the adjacent channels and the joint line is not formed in the central area of the chamber outer wall of the magazine. The joint line is therefore not positioned in the center between two adjacent partition wall channels in any case. However, it may be positioned in the edge areas between two adjacent partition wall channels, so that the joint lines are positioned at the edge (edge area) of the chamber outer wall of the magazine. The joint lines may also lie on the transition to the partition wall channel. It is important that a transparent area in the chamber outer wall of the magazine between two adjacent partition wall channels is not interfered with by a joint line. A transparent area which is positioned centrally between two adjacent partition wall channels is therefore preferably free of joint lines.

The plastic compound streams preferably flow together in the outer wall channel in such a manner that the joint line aligns with a partition wall channel. The joint lines are therefore positioned so that they are positioned in the area of the width of the partition wall channel, for example, centered or off-center to the partition wall channel. However, they may also be positioned at the boundary or the transition between partition wall channel and the area of the outer wall channel which later corresponds to the chamber outer wall of the magazine.

In a preferred embodiment, the flow speeds in two adjacent partition wall channels are set in such a manner that the joint line forms at the end of the partition wall channel in which the flow speed is less.

An essential feature for determining the position of the joint line on the outer wall channel is therefore the differing flow speed of the plastic compound stream in the channels. It may be influenced in various manners. For example, the plastic compound can be injected into individual partition wall channels using a higher pressure than in other partition wall channels. The flow speed may also be varied through the properties of the plastic compound. The flow speed of a plastic is typically strongly dependent on its temperature. Thus, for example, the plastic compound flowing through a specific partition wall channel may be hotter than the compound flowing through another channel. In this manner, an increase of the flow speed would occur. The heating of individual plastic compound streams in specific partition wall channels may be achieved by additional heating of individual partition wall channels, for example. For example, a heating wire may be attached in proximity to the channels. Heating by infrared radiation, another radiation, or other heating sources is also conceivable.

A further parameter for influencing and controlling the flow speed in the partition wall channels is the geometry of the partition wall channels. Adjacent partition wall channels in the casting mold are therefore preferably alternately wider and narrower. As a result, a wider channel and a narrower channel al-ternate. The flow speed in the wider partition wall channel, in which the flow resistance is less, is therefore higher.

The terms "wider" and "narrower" only relate to one spatial direction. In an-other spatial direction, the channels may definitely have different dimensions, for example, the partition wall channel which is wider in the decisive spatial direction (transversely to the flow direction between the side walls of the partition wall channels) may definitely be narrower in another spatial direction than its adjacent channel or vice versa. It is only important that the plastic com-pound can flow more rapidly through the wider partition wall channel than through the narrower partition wall channel.

If the adjacent partition wall channels are formed wider or narrower, the joint line of the plastic streams forms in the outer wall channel in the area of the narrower partition wall channels. The joint lines therefore align with the narrower partition wall channel. The joint lines are located on the outside of the outer wall channel within an area which results in the extension of the partition wall of the narrower partition wall channel.

In addition, it is also conceivable to coat the partition wall channels on the sides in order to increase or decrease the flow resistance, in order to thus take influence on the flow speed.

In a preferred embodiment, the width of the wider partition wall channels is 1.5 to 2.5 times as great as the width of the narrower partition wall channels. The width of the wider partition wall channels is preferably in the range of 1.5 times to 2.0 times the width of the narrower channels, it is particularly preferably 1.6 times as wide. The width ratio of the narrower and wider partition wall channels depends on the plastic material used.

In a preferred embodiment, the method according to the invention is implemented using a cylindrical casting mold. The casting mold in the form of a cylinder is used to produce a drum-shaped, in particular cylindrical magazine. In such a casting mold, the gate opening to permit the plastic compound to flow in is aligned with the rotational axis of the magazine. A uniform distribution of the plastic compound results through this central gate point. The plastic corn-pound flows through the partition wall channels, which extend radially outward, to the outer wall channel forming the lateral surface of the magazine. The compound flowing through adjacent partition wall channels then meets in the area of the partition wall channels oriented radially outward.

A two-part casting mold has proven to be advantageous. The first part is particularly preferably an outer part which is open on at least one side, and which has an outer wall. This open outer part preferably also has the central gate point for injecting the plastic compound into the casting mold. The second part is an inner part which has a lid, which terminates the open side of the outer part. Of course, the inner part could also have the central gate point.

It has proven to be advantageous for the inner part to comprise blocks, between which the partition wall channels are formed. The blocks of the inner part are positioned so that they extend into the outer part. Each block of the casting mold later corresponds to one chamber of the magazine. In the cylindrical casting mold for producing a (rotationally-symmetric) drum magazine, the blocks are positioned in such a manner that the partition wall channels extend radially outward. The blocks preferably have a trapezoidal cross-section, their width widening (increasing) toward the outer side of the casting mold.

Of course, it is also possible to produce cuboid magazines or magazines having other shapes using the method according to the invention. It is only important that the plastic compound flows from a gate point to an outer wall channel, the plastic compound curing in the outer wall channel later forming the outer wall of the magazine. In the case of oblong casting molds and therefore oblong magazines, the gate point having gate opening can also be formed as oblong. It is also possible to provide a plurality of gate points or a plurality of gate openings. In this manner, a uniform flow through the partition wall channels may be achieved, so that the flowing together of the plastic compound streams in the area of the partition wall channels in the outer wall channel is ensured.

The plastic compound which is used in the method according to the invention is transparent after curing. In a preferred embodiment, the plastic compound is also already transparent in the liquid or viscous state, i.e., when it is heated and injected into the casting mold. The plastic must have a composition such that an optical evaluation is possible through the plastic material.

A magazine is preferably produced using the method according to the invention, whose chambers are each used to receive one analysis element, which has an optically analyzable test zone. An optically measurable change occurs in the test zone as a reaction of a body fluid with a reagent of the analysis element. The change can be measured using an optical measuring unit positioned outside the magazine through the outer wall of the chamber and there-fore through the outer wall of the magazine.

It was recognized in the context of the invention that the plastic compound is preferably to be a transparent polymer material. A cycloolefin copolymer is particularly preferably used for this purpose. Such a material has a high transparency. An optical measurement through the outer wall of the transparent magazine is therefore possible, without the material resulting in influence of the measurement result.

Because of the method in which the plastic compound flows at differing flow speed through adjacent partition wall channels and in which the joint lines in the outer wall of the magazine align with the partition walls between adjacent chambers, the outer wall is free of joint lines in the area of the chamber. An interference-free optical evaluation of an analysis element positioned in the chambers may thus be implemented.

The invention is explained in greater detail hereafter on the basis of exemplary preferred embodiments shown in the figures. The special features shown therein may be used individually or in combination to provide other embodiments of the invention. The described embodiments do not represent a restriction of the generality of the subject matter defined in the claims.

DRAWINGS

DETAILED DESCRIPTION

The following description of technology is merely exemplary in nature of the subject matter, manufacture and use of one or more inventions, and is not intended to limit the scope, application, or uses of any specific invention claimed in this application or in such other applications as may be filed claiming priority to this application, or patents issuing therefrom.

Figure 1:
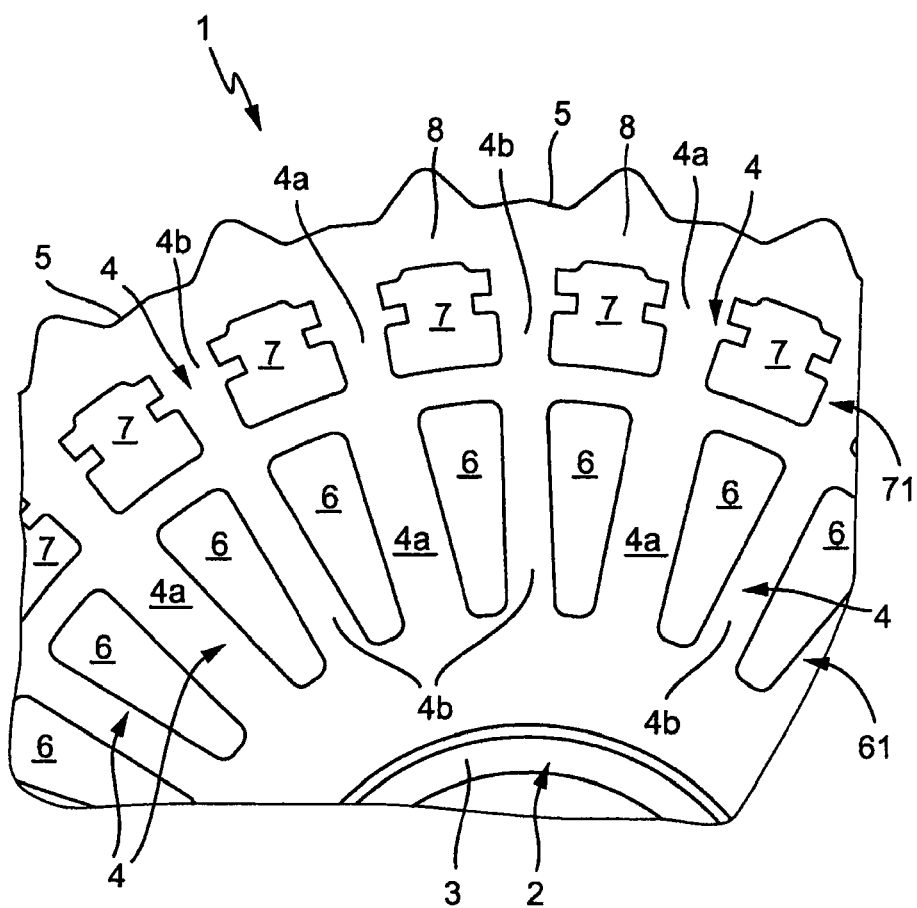
FIG. 1 shows a sectional view of a casting mold for the application of the production method according to the invention.

FIG. 1 shows a detail of a sectional view through a casting mold 1, using which a magazine according to the invention can be produced. The casting mold 1 is implemented as drum-shaped. A gate point 2 having gate opening 3 is aligned with the rotational axis of the casting mold 1. A heated, at least viscous plastic compound is injected into the casting mold 1 through the central gate opening 3. The plastic compound propagates via partition wall channels 4, which extend radially from the casting opening 3 to an outer wall 5 of the casting mold 1.

The partition wall channels 4 are formed by blocks 6, 7, which are positioned in two ring-shaped rows 61, 71. The blocks 6 of the inner ring 61 extend radially outward and are essentially elongate. They later form chambers in the magazine, which may be provided for receiving desiccant or which remain empty and therefore reduce the total weight of the magazine, for example. The blocks 7 of the outer ring 71 have a profiled contour in cross-section. They form chambers in the magazine to be produced for receiving analysis elements. An outer wall channel 8, which connects the individual partition wall channels 4 to one another, is formed between the outer ring 71 of blocks 7 and the outer wall 5.

The blocks 6, 7 are positioned in such a manner that partition wall channels 4a, 4b of different widths are formed, the channels 4a, 4b being positioned alternately. The inflowing plastic compound flows more rapidly through the wider partition wall channels 4a than through the narrower partition wall channels 4b, so that the plastic compounds flow together in the outer wall channel 8 in such a manner that the line formed because of the flowing together is aligned with the narrower partition wall channels 4b.

Figure 2:
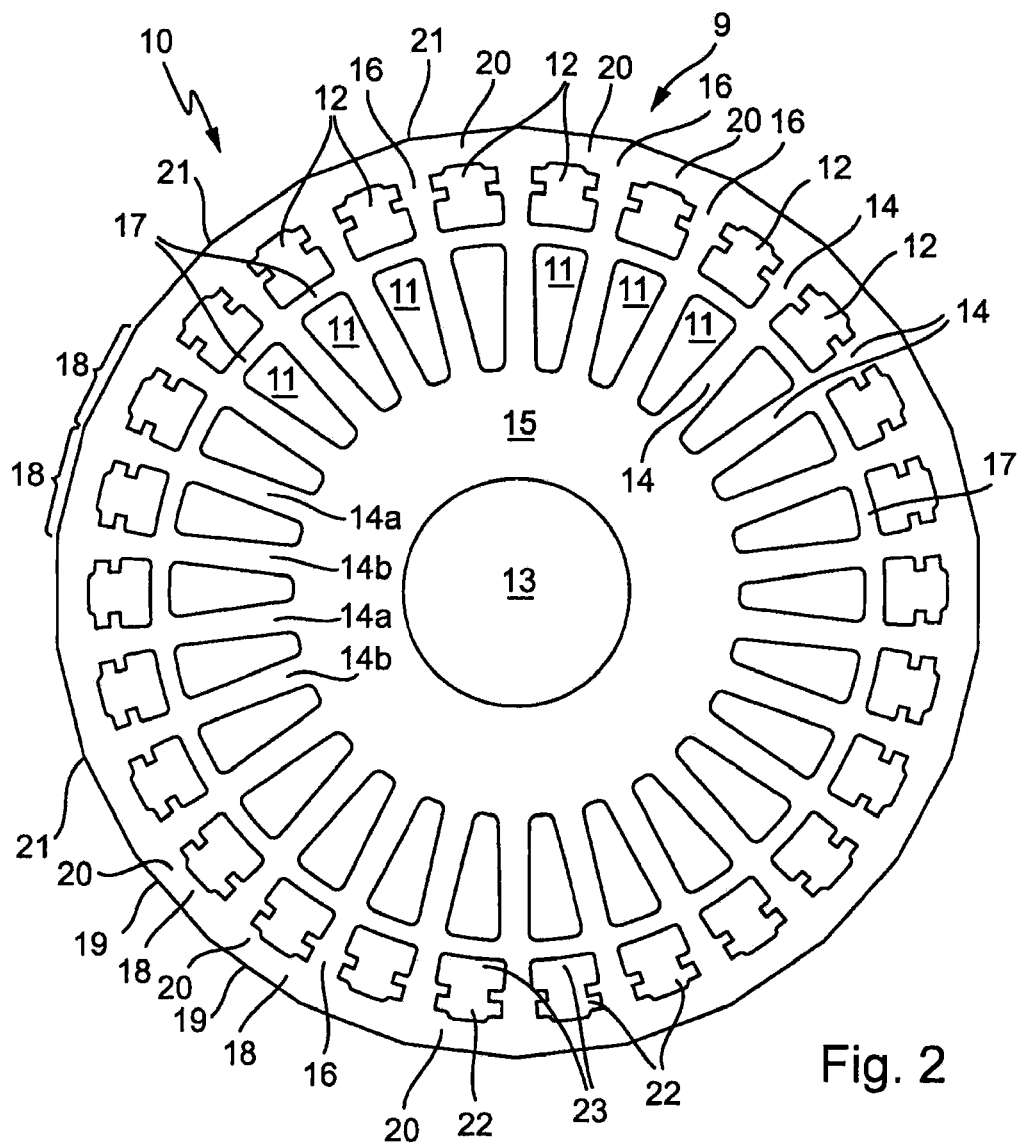
FIG. 2 shows a section through a magazine according to the invention.

The result of the magazine 10 produced using the casting mold 1 is a drum magazine 9, which is shown as a sectional view in FIG. 2. The blocks 6, 7 provided in the casting mold 1 now form the chambers 11 in an inner ring and the chambers 12 in an outer ring, which are positioned in a ring shape. A shaft for mounting and moving the magazine 10 can extend through a central rotation opening 13.

Partition walls 14 extend radially outward between respective adjacent chambers 11 and respective adjacent chambers 12. The partition walls 14 connect an inner magazine part 15 (between the rotation opening 13 and the inner ring formed from chambers 11) to an outer wall 16 of the magazine. Middle webs 17, which are positioned in a ring shape, and which connect the partition walls 14 to one another in the peripheral direction (i.e., transversely to the radial direction), extend between the inner chambers 11 and the outer chambers 12 (which are aligned adjacent in the radial direction).

The partition wall 14 thus forms a web between the respective adjacent chambers 11 or 12. Each partition wall 14 is a side wall for two chambers 11, 12 having two opposing lateral surfaces, which each form the lateral surface of one chamber 11, 12. Each of the chambers 12 has a chamber outer wall 20, which is part of the outer wall 16 of the magazine 10. The partition walls 14 adjoin the chamber outer wall 20.

The chamber outer walls 20 are preferably linear. They are part of a (flat) outer segment 18, the adjacent outer segments 18 preferably abutting at a joint line 21, at which the plastic compounds meet during the production process. The joint lines 21 are aligned with the partition walls 14 of the magazine 10 in this case. They may be seen at least on the outer lateral surface of the drum magazine 9.

The outer wall 16 of the drum magazine 9 is sectionally flat, so that the lateral surface of the drum magazine 9 is not a cylindrical lateral surface in the embodiment shown here. The flat outer segments 18 are implemented as planar, so that the magazine outer surfaces 19 of the outer segments 18 are parallel to the chamber outer walls 20 of the chambers 12. As may be seen clearly in FIG. 2, each two adjacent partition walls 14 are of different widths. A wide partition wall 14a and a narrow partition wall 14b continuously alternate with one another. The joint lines 21 are only positioned in the area of the narrow partition walls 14b. The magazine 10 preferably has an even number of chambers 12, in the example shown, twenty-six chambers 12 are adjacent to one another.

The chambers 12 are suitable for receiving analysis elements (not shown here) having an optically analyzable test zone. The analysis elements are positioned in an outer partial chamber 22 of the chamber 12. Its test zone is oriented so that it faces toward the chamber outer wall 20. Since the outer wall 16 of the magazine 10, preferably the entire magazine 10, is transparent and the outer wall 16 is free of joint lines 21 in the area of the chamber outer walls 20, an optical measurement through the chamber outer wall 20 is possible, in order to measure a measurable change in the test zone of the analysis element.

A second partial chamber 23 of the chamber 12 forms a free space in which a piercing element can be positioned or through which a piercing element can be moved.

The chambers 11 are separated from the chambers 12 in the plane of the magazine 10 shown in section here. If the chambers 11 are used to receive desiccant, they are connected to the respective adjacent chamber 12 in another plane of the magazine 10 in such a manner that moisture in the chambers 12 can be absorbed by the desiccant in the chambers 11. An air connection therefore exists between the chambers 11 and 12.

Figure 3:
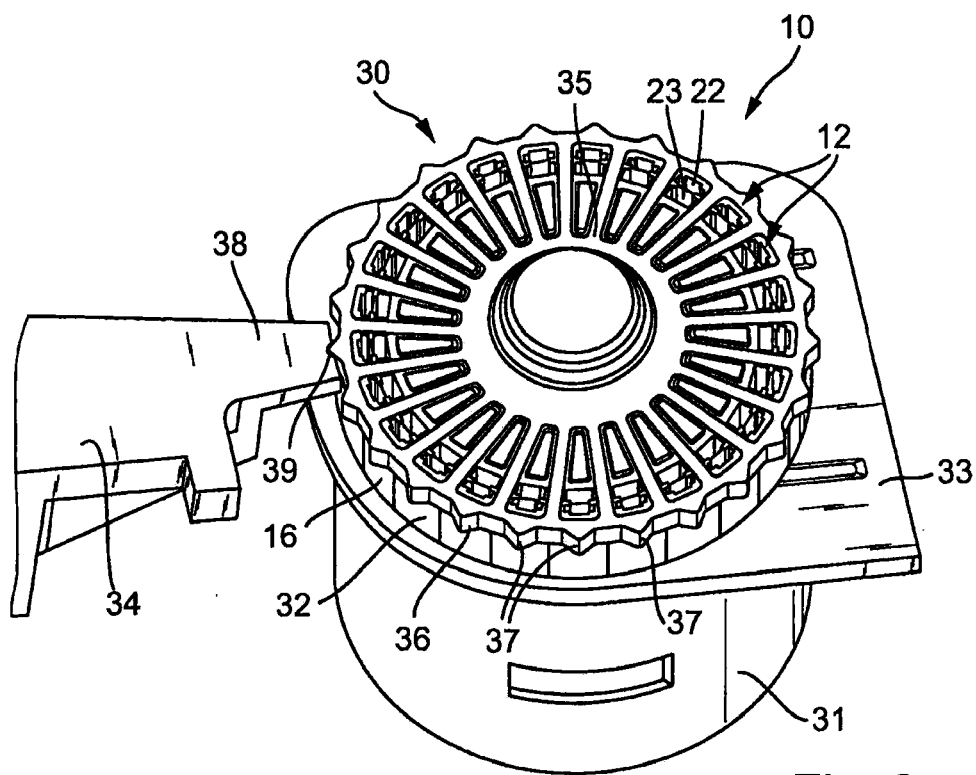
FIG. 3 shows a two-part magazine which has been produced using the method according to the invention.

FIG. 3 shows a two-part drum magazine 30 having a piercing element partial magazine 31 and an analysis element partial magazine 32, which is the magazine 10 from FIG. 2 produced using the method according to the invention. The two partial magazines 31, 32 are spaced apart from one another in the axial direction. A so-called contact pressure element 33 is positioned between them, which is displaceable transversely to the axial direction of the drum magazine 30.

The piercing element partial magazine 31 has piercing element chambers adjacent to one another, each of which contains a piercing element. The piercing elements are axially oriented and may be moved in the axial direction in such a manner that they are moved through the analysis element partial magazine 32 and exit on its upper, free front side 35.

During the piercing movement of the piercing element out of the piercing element partial magazine 31 through the analysis element partial magazine 32, the piercing element is moved in the partial chamber 32 of the chamber 12, which is close to the rotational axis. During the retraction phase of the piercing movement, it is moved back axially far enough that a transfer zone of the piercing element is adjacent to an analysis element positioned in the partial chamber 22. A movement of the contact pressure element 33 presses the piercing element against the analysis element, so that the body fluid obtained during the piercing movement is transferred onto the analysis element.

The transferred body fluid induces an optically measurable change in the analysis element, which can be measured using a photoelectric measuring unit 34. The analysis element partial magazine 32 has a gear ring 36, which is positioned on the magazine outer wall 16, having a plurality of teeth 37 in its area adjacent to the forward front side 35. The teeth 37 are used as positioning elements, to position the optical measuring unit 34 reliably and reproducibly on the magazine 10. The measuring unit 34 has a positioning arm 38 having a positioning contour 39, which corresponds with the teeth 37, for this purpose.

For further details with respect to the two-part drum magazine 30, reference is made to the European patent application having the application number EP 08010403, whose content is made part of the content of this application by reference.

Figure 4:
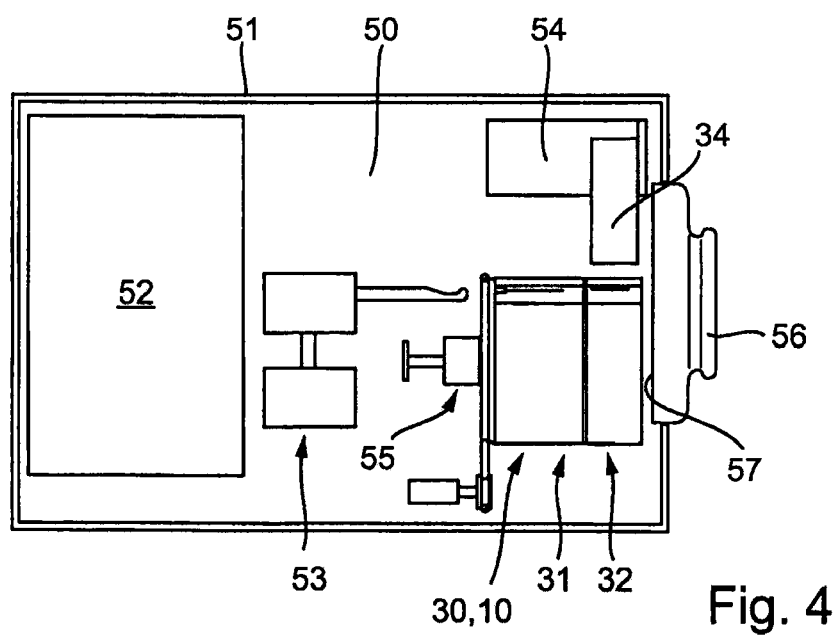
FIG. 4 shows an analysis device having a magazine according to the invention for disposable integrated piercing and analysis elements.

Finally, FIG. 4 shows the magazine 10, which is positioned in an analysis device 50 having a housing 51, a power supply 52, a piercing drive 53, and a measuring and evaluation unit 54, which includes the photoelectric measuring unit 34. A mount 55 is used for receiving the two-part drum magazine 30, which is positioned so that piercing elements exiting on the front side 35 may create a wound in a body part which presses against a skin contact ring 56 on a housing opening 57. More details on the operation of the analysis device 50 and the magazine 10, 30 can be inferred from the patent application having the application number EP 08010403.

LIST OF REFERENCE NUMERALS 1 casting mold
2 gate point
3 gate opening
4 partition wall channel
5 outer wall
6 block
7 block
8 outer wall channel
9 drum magazine
10 magazine
11,12 chamber
13 rotation opening
14 partition wall
15 inner part
16 outer wall
17 middle web
18 outer segment
19 magazine outer surface
20 chamber outer wall
21 joint line
22 partial chamber
23 partial chamber
30 two-part drum magazine
31 piercing element partial magazine
32 analysis element partial magazine
33 contact pressure element
34 photoelectric measuring unit
35 front side (of 30, 10)
36 gear ring
37 tooth
38 positioning arm
39 positioning contour
50 analysis device
51 housing
52 power supply
53 piercing drive
54 measuring and evaluation unit
55 mount
56 skin contact ring
57 housing opening

What is claimed is:
1. A monolithic magazine for an analysis device having a plurality of chambers and an integral outer wall,
the plurality of chambers being positioned adjacent to one another and each of the plurality of chambers having a chamber outer wall, which is part of the integral outer wall of the magazine,
each of the plurality of chambers having two adjacent partition walls,
the magazine being produced using injection-molding methods,
the integral outer wall of the magazine being transparent in the area of the chamber outer walls, the magazine having joint lines on the integral outer wall, the joint lines being positioned outside a middle of the chamber outer wall, which extends between the two adjacent partition walls;

wherein the two adjacent partition walls of each chamber comprise different thicknesses.

2. The magazine according to claim 1, wherein the joint lines are aligned with the partition walls of the chambers.

3. The magazine according to claim 1, wherein the magazine is a drum magazine.

4. The magazine according to claim 1, wherein the entire magazine is transparent.

5. The magazine according to claim 1, wherein the chambers are suitable for receiving analysis elements having an optically analyzable test zone, an optically measurable change occurring on the test zone as a reaction of a bodily fluid with a reagent of the analysis elements, wherein the chamber outer wall is operable to allow measurement of the change through the integral outer wall using a photoelectric measuring unit.

6. The magazine according to claim 1, wherein the magazine is made by an injection molding process using a casting mold having an outer wall channel, which corresponds to the outer wall of the magazine, and partition wall channels, which correspond to the partition walls, and having a gate opening, a plurality of partition wall channels extending from the gate opening to the outer wall channel; the process comprising:

injecting a plastic compound, which is transparent at least after curing, into the gate opening, causing the plastic compound to flow as a plastic compound stream from the gate point through the partition wall channels into the outer wall channel in such a manner that the plastic compound streams have a differing flow speed in alternating rotational channels, flowing together of the plastic compound streams in the outer wall channel in such a manner that a joint line forms on the outer side of the outer wall channel, which is positioned so that it is not positioned in the center between two adjacent partition wall channels.

* * * * *